(12) United States Patent
Bobba Venkata et al.

(10) Patent No.: US 9,409,913 B2
(45) Date of Patent: Aug. 9, 2016

(54) POLYMORPHIC FORMS OF ALCAFTADINE

(71) Applicant: Enaltec Labs Pvt. Ltd., Sanpada, Navi Mumbai (IN)

(72) Inventors: Sivakumar Bobba Venkata, Maharashtra (IN); Eswara Rao Kodali, Maharashtra (IN); Girish Bansilal Patel, Maharashtra (IN); Sanjay Dashrath Vaidya, Maharashtra (IN); Alok Pramod Tripathi, Maharashtra (IN)

(73) Assignee: ENALTEC LABS PRIVATE LIMITED, Navi Mumbai (IN)

( * ) Notice: Subject to any disclaimer, the term of this patent is extended or adjusted under 35 U.S.C. 154(b) by 109 days.

(21) Appl. No.: 14/370,801

(22) PCT Filed: Nov. 14, 2013

(86) PCT No.: PCT/IB2013/002510
§ 371 (c)(1),
(2) Date: Jul. 7, 2014

(87) PCT Pub. No.: WO2014/080259
PCT Pub. Date: May 30, 2014

(65) Prior Publication Data
US 2015/0080376 A1    Mar. 19, 2015

(30) Foreign Application Priority Data
Nov. 21, 2012 (IN) .......................... 3334/MUM/2012

(51) Int. Cl.
*A61K 31/55* (2006.01)
*C07D 487/04* (2006.01)
*C07D 403/04* (2006.01)

(52) U.S. Cl.
CPC .............. *C07D 487/04* (2013.01); *A61K 31/55* (2013.01); *C07D 403/04* (2013.01)

(58) Field of Classification Search
CPC .............................. A61K 31/55; C07D 487/04
USPC ...................... 514/214.02; 540/579
See application file for complete search history.

(56) References Cited

U.S. PATENT DOCUMENTS 5,468,743 A    11/1995    Janssens et al.

FOREIGN PATENT DOCUMENTS

WO    WO 2007/117971    * 10/2007

* cited by examiner

*Primary Examiner* — Brenda Coleman
(74) *Attorney, Agent, or Firm* — Bruzga & Associates; Charles E. Bruzga; Jay S. Pattumudi

(57) ABSTRACT

The present invention relates to novel polymorphic forms of alcaftadine, processes of preparing novel polymorphic forms of alcaftadine and pharmaceutical compositions thereof.

8 Claims, 5 Drawing Sheets

POLYMORPHIC FORMS OF ALCAFTADINE

FIELD OF THE INVENTION

The present invention relates to novel polymorphic forms of alcaftadine. The present invention further relates to processes of preparing novel polymorphic forms of alcaftadine and pharmaceutical composition thereof.

BACKGROUND OF THE INVENTION

Alcaftadine is chemically 6,11-dihydro-11-(1-methyl-4-piperidinylidene)-5H-imidazo[2,1-b][3]benzazepine-3-carboxaldehyde and is known from U.S. Pat. No. 5,468,743 and is represented by a compound of structural formula I:

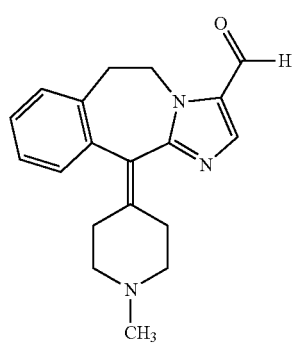

Formula I

Alcaftadine is a $H_1$ histamine receptor antagonist sold in USA under the proprietary name of "LASTACAFT" and is indicated for the prevention of itching associated with allergic conjunctivitis.

The process of preparing alcaftadine compound of structural formula I is disclosed in U.S. Pat. No. 5,468,743 for preparing "alcaftadine analogous compound," which is represented below in Scheme no. I, Scheme no. II and Scheme no. III. The alcaftadine obtained according to Scheme no. I, Scheme no. II and Scheme no. III is characterized by melting point of 171.6° C. (referred herein after as Form I).

Scheme I

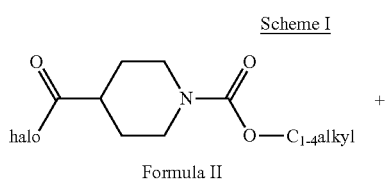

Formula II

+

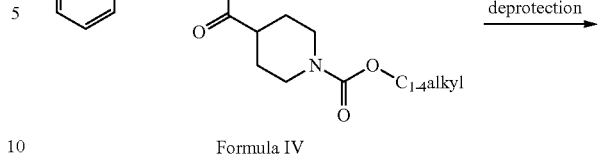

Formula III

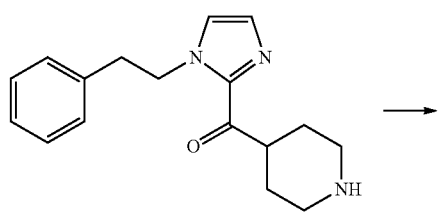

Formula IV

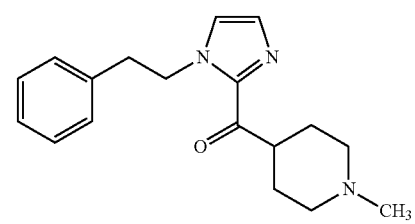

Formula V

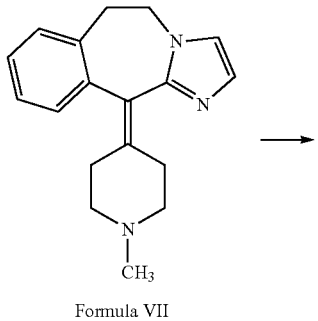

Formula VI

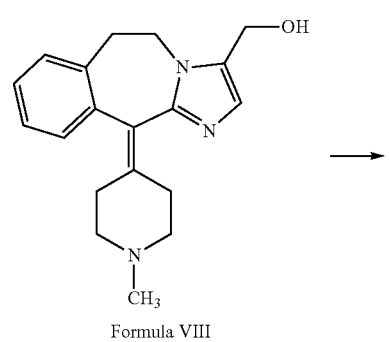

Formula VII

Formula VIII

US 9,409,913 B2

3
-continued

Formula I

Scheme II

Formula IX
+
Formula III
→
Formula X
48% HBr
→
Formula XI ·2HBr
Trifluoromethane sulfonic acid (E)-2-butenedioate (1:2)
→
Formula XII ·(E)-2-butenedioate (1:2)

4
-continued

Formula VII
→
Formula VIII
→
Formula I

Scheme III

Formula XIII
+
Formula III
→
Formula VI
→

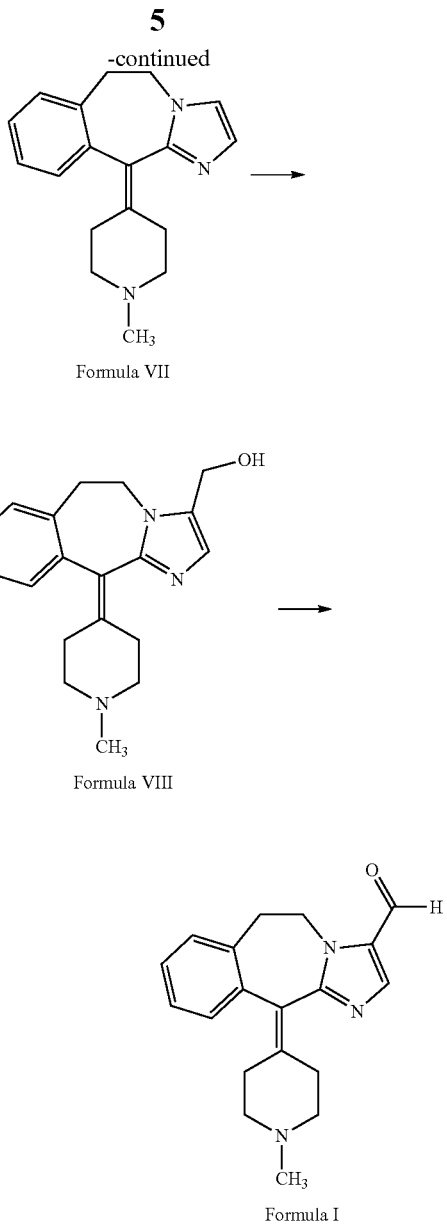

Formula VII

Formula VIII

Formula I

A survey of the literature on alcaftadine did not provide any reference to its crystal structure or the possibility of different polymorphs. Information about the solid-state properties of a drug substance is important. For example, different forms may have significantly different solubilities. Further, the handling and stability of a drug substance may depend critically on the solid state of the drug.

Polymorphism is defined as "the ability of a compound to crystallize in more than one distinct crystal species" and different crystal arrangements of the same chemical compound are termed as polymorphs. Polymorphs of the same compound arise due to difference in the internal arrangement of atoms. Different polymorphs have different free energies and therefore have different physical properties such as solubility, chemical stability, melting point, density, flow properties, bioavailability and so forth.

The inventors of the present application have found that alcaftadine can exhibit polymorphism (i.e., alcaftadine can exist in different polymorphic forms) and accordingly, novel polymorphic forms of alcaftadine are provided.

SUMMARY OF THE INVENTION

A first aspect of the present invention is to provide novel polymorphic forms of alcaftadine.

According to another aspect, the present invention relates to crystalline forms of alcaftadine.

According to another aspect, the present invention relates to an α-crystalline form of alcaftadine.

According to another aspect, the present invention relates to a process for the preparation of α-crystalline form of alcaftadine.

According to another aspect, the present invention relates to a process of preparing α-crystalline form of alcaftadine comprising the steps of:
  a. suspending crude alcaftadine in an organic solvent,
  b. stirring suspension obtained in step-a and,
  c. isolating an α-crystalline form of alcaftadine.

According to another aspect, the present invention relates to a process of preparing α-crystalline form of alcaftadine comprising the steps of:
  a. suspending crude alcaftadine in a ketone solvent,
  b. stirring suspension obtained in step-a and,
  c. isolating α-crystalline form of alcaftadine.

According to another aspect, the present invention relates to a β-crystalline form of alcaftadine.

According to another aspect, the present invention relates to process for the preparation of β-crystalline form of alcaftadine.

According to another aspect, the present invention relates to a process of preparing β-crystalline form of alcaftadine comprising the steps of:
  a. suspending crude alcaftadine in an ether solvent to obtain a suspension;
  b. stirring the suspension obtained in the step of suspending crude alcaftadine;
  c. isolating a β-crystalline form of alcaftadine.

Another aspect of the present invention is to provide amorphous form of alcaftadine.

Another aspect of the present invention is to provide process for the preparation of amorphous form of alcaftadine.

Another aspect of the present invention is to provide a process of preparing amorphous form of alcaftadine comprising, the steps of:
  a. preparing a solution of alcaftadine in an organic solvent and
  b. recovering alcaftadine in the amorphous form from said solution by removing solvent by using techniques selected from the group comprising of spray-drying or freeze-drying.

Another aspect of the present invention is to provide a process of preparing amorphous form of alcaftadine comprising the steps of:
  a. preparing a solution of alcaftadine in an organic solvent,
  b. removing the solvent from the solution obtained in step-a by using agitated thin film drying, and
  c. recovering alcaftadine in the amorphous form from the agitated thin film dryer.

Another aspect of the present invention is to provide a process of preparing amorphous form of alcaftadine comprising the steps of:
  a. melting crystalline form of alcaftadine and
  b. recovering alcaftadine in an amorphous form.

Another aspect of the present invention is to provide a pharmaceutical composition comprising α-crystalline form of alcaftadine.

Another aspect of the present invention is to provide a pharmaceutical composition comprising β-crystalline form of alcaftadine.

Another aspect of the present invention is to provide pharmaceutical composition comprising amorphous form of alcaftadine.

BRIEF DESCRIPTION OF THE DRAWINGS

Further features and advantages of the invention will become apparent from reading the following detailed description in conjunction with the following drawings, in which like reference numbers refer to like parts.

DETAILED DESCRIPTION OF THE INVENTION

The examples and drawings provided in the detailed description are merely exemplary, and should not be used to limit the scope of the claims in any claim construction or interpretation.

The present invention relates to novel polymorphic forms of alcaftadine and process for the preparation thereof.

The present invention further relates to α-crystalline form of alcaftadine characterized by X-ray diffraction pattern having peaks at 8.3, 10.9, 12.7, 14.7, 15.1, 15.4, 16.0, 16.5, 17.2, 17.7, 18.7, 19.1, 19.9, 21.1, 22.0, 22.7, 24.1, 24.7, 25.1, 26.3, 26.7, 27.2, 28.0, 28.5±0.2 degrees 2θ.

Figure 1:
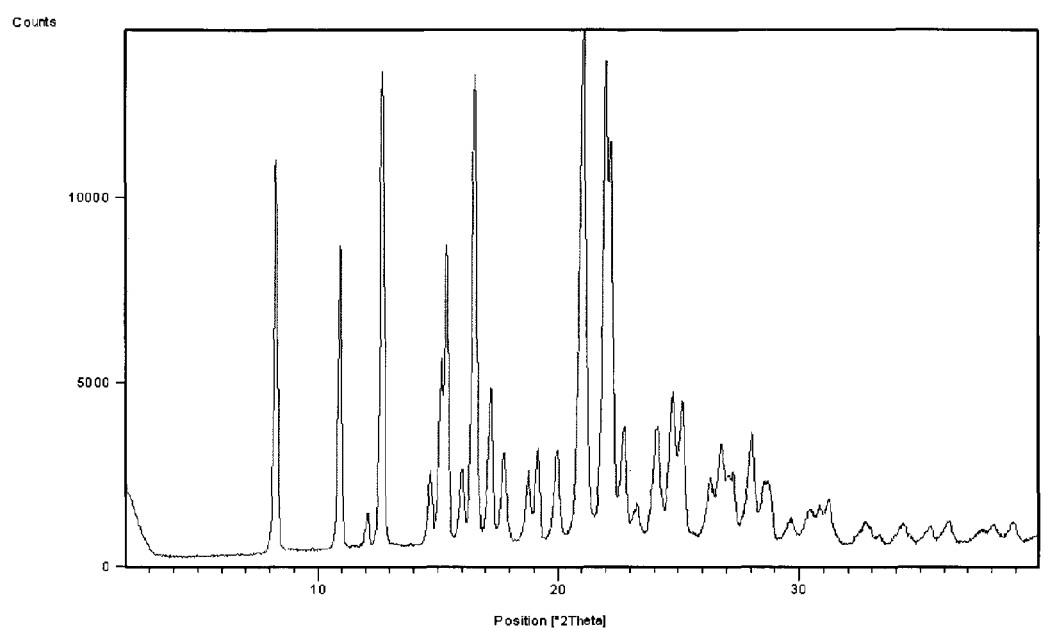
FIG. 1 depicts an X-ray diffraction pattern of α-crystalline form of alcaftadine.

In another embodiment, the present invention relates to α-crystalline form of alcaftadine characterized by an X-ray diffraction pattern as depicted in FIG. 1.

Figure 2:
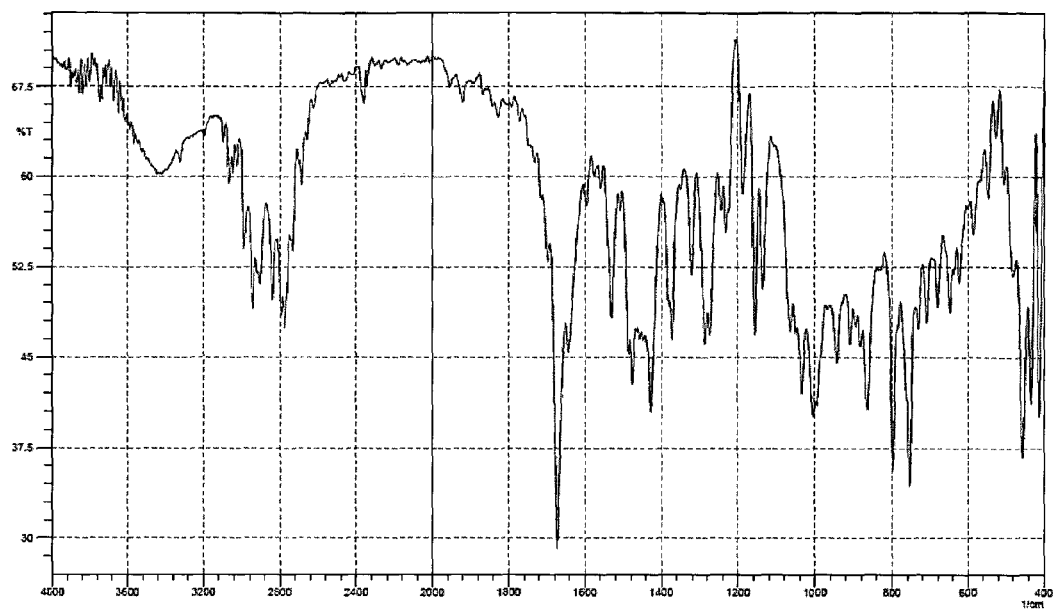
FIG. 2 depicts an infrared spectra of α-crystalline form of alcaftadine.

In another embodiment, the present invention relates to α-crystalline form of alcaftadine characterized by an infrared spectrum as depicted in FIG. 2.

In another embodiment, the present invention relates to β-crystalline form of alcaftadine characterized by an X-ray diffraction pattern having peaks at 10.0, 11.4, 12.0, 15.5, 16.2, 18.4, 19.6, 20.2, 20.5, 22.0, 23.1, 23.5, 24.6, 25.4, 25.8, 28.8, 31.3±0.2 degrees 2θ.

Figure 3:
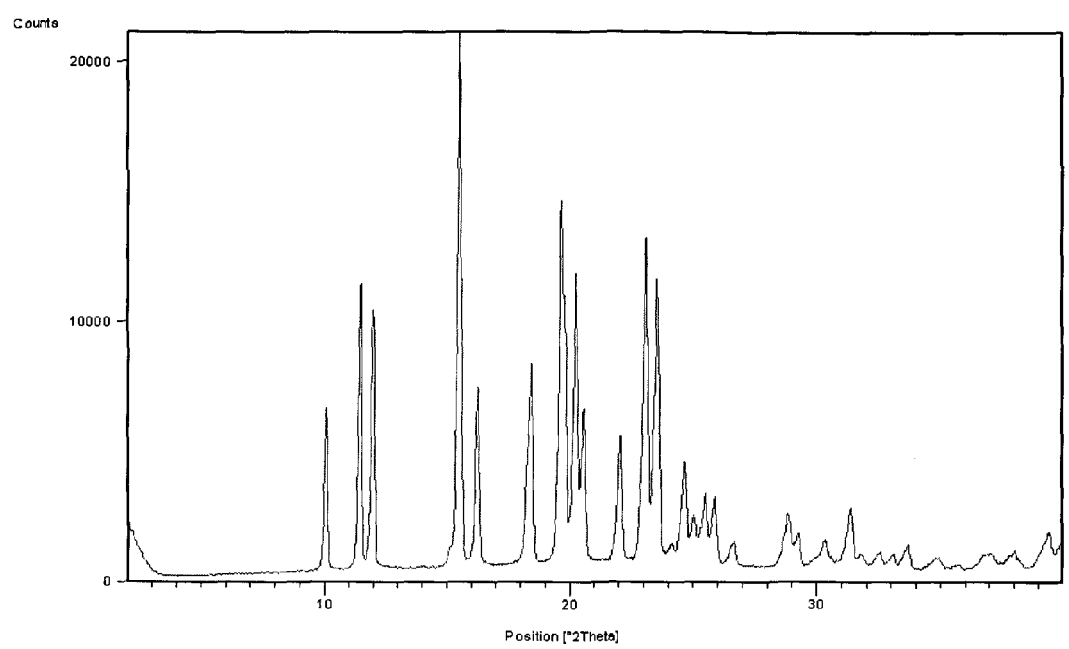
FIG. 3 depicts an X-ray diffraction pattern of β-crystalline form of alcaftadine.

In another embodiment, the present invention relates to β-crystalline form of alcaftadine characterized by an X-ray diffraction pattern as depicted in FIG. 3.

Figure 4:
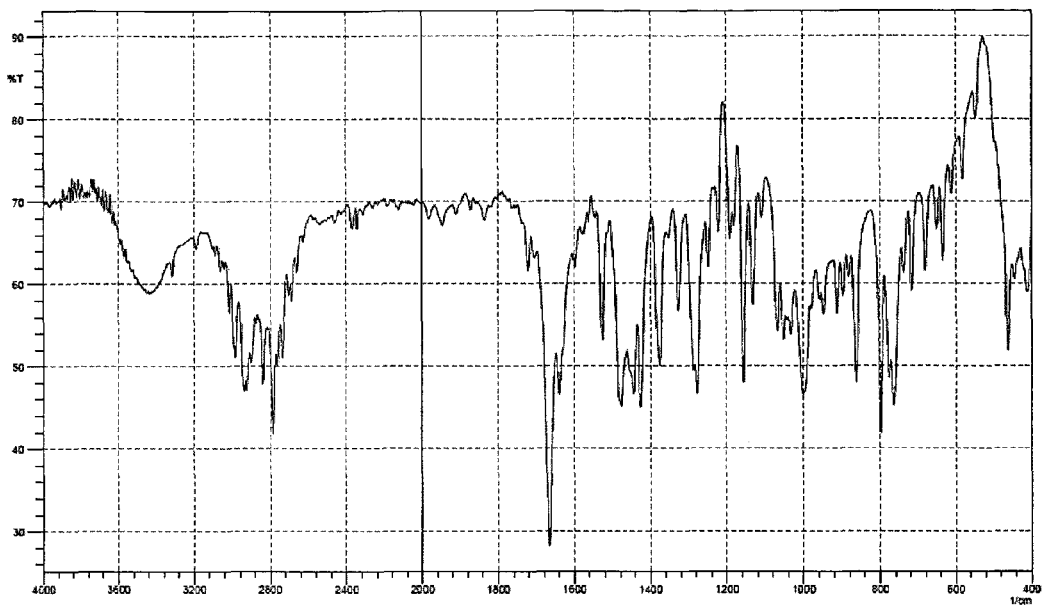
FIG. 4 depicts an infrared spectra of β-crystalline form of alcaftadine.

In another embodiment, the present invention relates to β-crystalline form of alcaftadine characterized by an infrared spectrum as depicted in FIG. 4.

Figure 5:
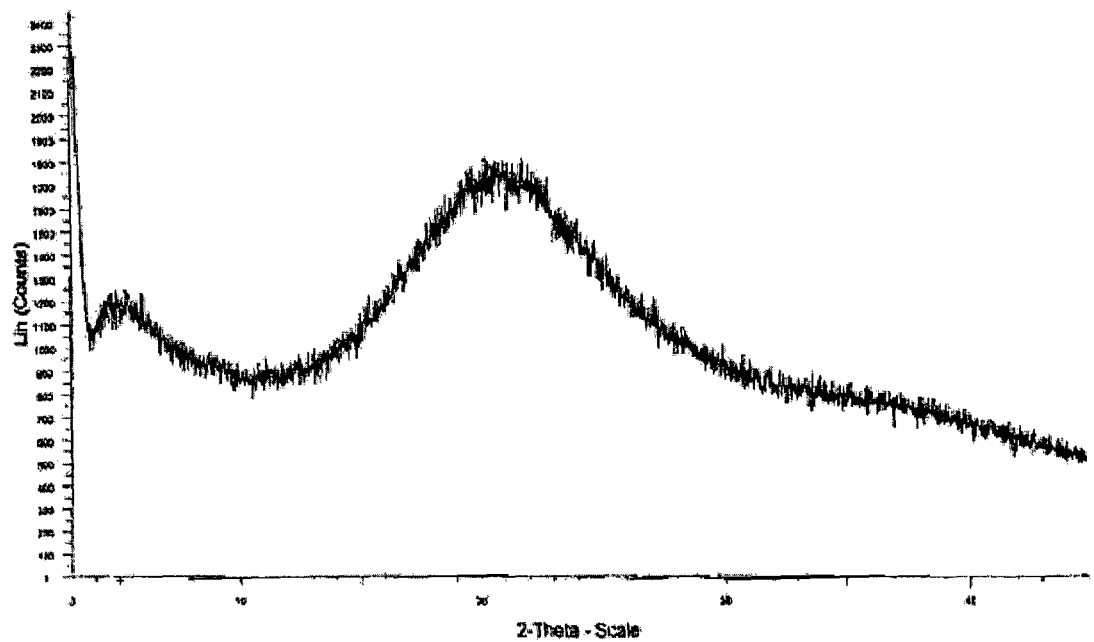
FIG. 5 depicts an X-ray diffraction pattern of amorphous form of alcaftadine.

In another embodiment, the present invention relates to an amorphous form of alcaftadine characterized by an X-ray diffraction pattern as depicted in FIG. 5.

The crude alcaftadine used according to the present invention can be prepared by methods disclosed in the art such as those described in U.S. Pat. No. 5,458,743, which is incorporated herein by reference.

The α-crystalline form of alcaftadine is prepared by suspending crude alcaftadine in an organic solvent, stirring the resulting suspension at a temperature in the range of 0° C. to 50° C. for a period in the range of 30 minutes to 6 hours and isolating the α-crystalline form of alcaftadine from the suspension.

The β-crystalline form of alcaftadine is prepared by suspending crude alcaftadine in an organic solvent, stirring the resulting suspension at a temperature in the range of 0° C. to 50° C. for a period in the range of 30 minutes to 8 hours and isolating the β-crystalline form of alcaftadine from the suspension.

An organic solvent according to the present invention can be selected from the group comprising, but not limited to, alcohols, furans, ethers, ketones, nitrites, esters, hydrocarbons such as halogenated aliphatic hydrocarbon solvents or the like or mixtures thereof. Ketone solvent can be selected from the group comprising, but not limited to acetone, methyl ethyl ketone, methyl isobutyl ketone, dibutyl ketone, diethyl ketone, dipropyl ketone, diisopropyl ketone, methyl butyl ketone, methyl propyl ketone, methyl isopropyl ketone, ethyl isopropyl ketone or mixture(s) thereof.

The ether solvent can be selected from the group comprising, but not limited to, tetrahydrofuran, dioxane, diethyl ether, diisopropyl ether, dibutyl ether, methyl tertiary butyl ether, methyl ethyl ether, methyl isobutyl ether or mixture(s) thereof.

The alcohol solvents can be selected from the group comprising, but not limited to, methanol, ethanol, propanol, isopropanol, butanol, isobutanol, t-butanol, pentanol or mixture(s) thereof.

The ester solvents can be selected from the group comprising, but not limited to, ethyl acetate, propyl acetate, isopropyl acetate, butyl acetate, tertiary butyl acetate, pentyl acetate or mixture(s) thereof.

The nitrite solvents can be selected from the group comprising, but not limited to, acetonitrile, propionitrile or mixture(s) thereof.

The halogenated aliphatic hydrocarbon solvents can be selected from the group comprising, but not limited to, dichloromethane, dichloroethane, chloroform, carbon tetrachloride or mixture(s) thereof.

The crystalline forms (α and/or β) of alcaftadine may be isolated by any known process in the art such as filtration, centrifugation, washing, drying or the combinations thereof.

The isolated crystalline forms (α and/or β) of alcaftadine may be dried at a temperature in the range of 40° C. to 110° C. for a period of 2 hours to 12 hours under reduced pressure.

A solution of crude alcaftadine in an organic solvent may be prepared by dissolving alcaftadine in an organic solvent at a temperature in the range of 20° C. to 60° C.

Alternatively, such a solution may be obtained directly from a reaction in which alcaftadine is formed.

In another embodiment according to present invention, the solvent may be removed from the solution by a technique which includes, for example, spray drying and freeze drying.

In one aspect, an alcaftadine amorphous form may be recovered from the solution using a spray drying technique. A Mini-Spray Dryer (Model: Buchi 190, Switzerland) can be used. The Buchi 190 Mini-Spray Dryer operates on the principle of nozzle spraying in a parallel flow (i.e., the sprayed product and the drying gas flow in the same direction). The drying gas can be air or inert gases such as nitrogen, argon and carbon dioxide.

In another aspect, an alcaftadine amorphous form may be recovered from the solution using a freeze drying technique. A freeze dryer (Model; Virtis Genesis SQ Freeze Dryer) can be used in this technique. The Virtis Genesis SQ Freeze Dryer operates on the principle of lyophilization, i.e., a process of stabilizing initially wet materials (aqueous solution or suspensions) by freezing them, then subliming the ice while simultaneously desorbing some of the bound moisture (primary drying). Following removal of the ice, desorption may be continued (secondary drying). This process may be carried out under vacuum.

The spray drying may be accomplished using a spray dryer which operates on the principle of nozzle spraying in a parallel flow, i.e., the sprayed product and the drying gas flow in the same direction. The drying gas can be air or one or more inert gases such as nitrogen, argon, and carbon dioxide. Moreover, the product obtained may be further or additionally dried to achieve the desired moisture values. For example, the product may be further or additionally dried in a tray drier, dried under vacuum and/or in a Fluid Bed Dryer.

The solution of alcaftadine may be optionally treated with activated charcoal and the resulting solution is filtered through hyflo bed to get filtrate.

The resulting filtrate is fed into an agitated thin film dryer (ATFD). The solvent is subsequently removed from the solution by agitated thin film drying.

The drying process may be accompanied by heating at a temperature in the range of 30° C. to 60° C. under reduced pressure.

The feeding rate of the solution may be controlled in such a way to facilitate the thin film formation and the evaporation rate. The rotor and vapor duct can have a sealing system so that the drying can preferably be carried under vacuum. Vacuum operation also facilitates amorphous form of alcaftadine to be obtained without degradation.

The crystalline form of alcaftadine may be melted at a temperature in the range of 160° C. to 190° C.

The alcaftadine amorphous form may be recovered by the steps of cooling and milling of melted alcaftadine. The milling of melted alcaftadine may be carried out in a mortar and pestle.

The cooling of melted alcaftadine may be carried out up to the temperature in the range of 20-30° C.

The term "recovering alcaftadine in the amorphous form," according to the present invention, includes unloading, amassing, gathering, scaling and/or piling amorphous form of alcaftadine.

The amorphous form of alcaftadine may be optionally further dried under vacuum at a temperature in the range of 40° C. to 110° C. for 2 hours to 8 hours to obtain amorphous form of alcaftadine with desired residual solvent content.

In another embodiment, the present invention relates to the pharmaceutical composition of alcaftadine comprising α-crystalline form of alcaftadine and one or more pharmaceutically acceptable excipients.

In another embodiment, the present invention relates to the pharmaceutical composition of alcaftadine comprising β-crystalline form of alcaftadine and one or more pharmaceutically acceptable excipients.

In another embodiment, the present invention relates to the pharmaceutical composition of alcaftadine comprising amorphous form of alcaftadine and one or more pharmaceutically acceptable excipients.

The pharmaceutical composition of alcaftadine may be in the form of an ophthalmic solution.

An ophthalmic solution of alcaftadine may have an alcaftadine active ingredient in the range of 0.05 to 0.25% weight/weight.

The pharmaceutical excipients may be selected from the group consisting of sodium phosphate, edetate disodium, benzalkonium chloride and sodium chloride.

The pH of an ophthalmic solution of alcaftadine may be adjusted by an aqueous solution of sodium hydroxide or hydrochloric acid.

An X-ray diffraction (XRD) measurement was performed on X-Ray powder diffractometer Bruker D8 Advance powder diffractometer with the detector Lynxeye (Bruker). The analysis conditions were as follows:
Scan range [° 2-theta]: 2-39.98;
Scan mode; Continuous;
Step size [° 2-theta]: 0.0170°;
Scan step time[s]: 51.04 seconds;
Sample spin: 15 rpm;
Sample holder: glass;
Measurement Temperature [° C.]: 25
Anode Material: Cu
K-Alpha [Å]: 1.54060

Prior to analysis, the samples were gently ground by means of mortar and pestle in order to obtain a fine powder. The sample might be mixed with n-dodecane in order to avoid the environment contamination by airborne particles coming from the powder. The ground sample or its suspension with n-dodecane was adjusted into a cavity of the sample holder and the surface of the sample was smoothed by means of a cover glass.

EXAMPLES

In the following examples, the preferred embodiments of the present invention are described only by way of illustrating the process of the invention. However, these are not intended to limit the scope of the present invention in any way.

Example 1

Preparation of α-crystalline form of Alcaftadine

Crude alcaftadine (10 grams) was suspended in acetone (30 ml) at 25° C. and resulting suspension was stirred for 3 hours at 25° C. The resulting solid was filtered, washed with acetone (10 ml) and then dried at 45° C. for 8 hours under reduced pressure.
Yield: 9.7 grams and Purity: 99.96% (By HPLC)
XRD: As depicted in FIG. 1.
IR: As depicted in FIG. 2.

Example 2

Preparation of β-crystalline form of Alcaftadine

Crude alcaftadine (10 grams) was suspended in diethyl ether (40 ml) at 25-30° C. and resulting suspension was stirred for 2 hours at 25° C. The resulting solid was filtered, washed with diethyl ether (10 ml) and then dried at 50° C. for 12 hours under reduced pressure.
Yield: 9.8 grams and Purity: 99.87% (By HPLC)
XRD: As depicted in FIG. 3.
IR: As depicted in FIG. 4.

Example 3

Preparation of Amorphous form of Alcaftadine

Crystalline alcaftadine (10 grams) was dissolved in isopropanol (60 ml) at 30-40° C. The clear solution was subjected to spray drying in a mini spray dryer at an inlet temperature of 80° C. and an outlet temperature of 50° C. with a feed rate of 15 ml/minute. Alcaftadine in an amorphous form was thus isolated.
Yield: 9.5 grams and purity: 99.97% (By HPLC)

Example 4

Preparation of Amorphous form of Alcaftadine

A solution of alcaftadine (100 grams) in methanol (1200 ml) was fed into an agitated thin film dryer at a vacuum in the range of 50-100 mm Hg and a jacket temperature in the range of 45-54° C. The obtained solid was dried under reduced pressure at a temperature of 70° C. for 5 hours to obtain amorphous alcaftadine.

Yield: 82 grams and Purity: 99.85% (By HPLC)

Example 5

Preparation of Amorphous form of Alcaftadine

A solution of alcaftadine (100 grams) in methanol (1200 ml) was treated with activated charcoal (10 grams) and the resulting solution was filtered through hyflo bed to get filtrate. The resulting filtrate was fed into an agitated thin film dryer at a vacuum in the range of 50-100 mm Hg and a jacket temperature in the range of 45-54° C. The obtained solid was dried in a vacuum tray dryer under reduced pressure at 70° C. for 6 hours to obtain amorphous alcaftadine.

Yield: 80 grams and Purity: 99.95% (By HPLC)

Example 6

Preparation of Amorphous form of Alcaftadine

A crystalline form of alcaftadine (10 grams) was placed in an oven at 175° C. for 45 minutes. The melted alcaftadine was cooled to 25° C. and then the obtained solid was milled in a mortar and pestle to obtain amorphous alcaftadine.

Yield: 9.8 grams and Purity: 99.94% (By HPLC)

The scope of the claims should not be limited by the preferred embodiments and examples, but should be given the broadest interpretation consistent with the specification as a whole.

The invention claimed is:

1. A β-crystalline form of alcaftadine having characteristics of X-ray diffraction peaks at 10.0, 11.4, 12.0, 15.5, 16.2, 18.4, 19.6, 20.2, 20.5, 22.0, 23.1, 23.5, 24.6, 25.4, 25.8, 28.8, 31.3±0.2 degrees 2θ.

2. A β-crystalline form of alcaftadine characterized by having substantially the same X-ray diffraction pattern as depicted in FIG. 3.

3. A β-crystalline form of alcaftadine characterized by having substantially the same infrared spectrum as depicted in FIG. 4.

4. A process of preparing a β-crystalline form of alcaftadine, the process comprising the steps of:
   a) suspending crude alcaftadine in an organic solvent to obtain a suspension;
   b) stirring the suspension obtained in the step of suspending crude alcaftadine; and
   c) isolating a β-crystalline form of alcaftadine.

5. The process according to claim 4, wherein the suspension obtained in the step of suspending crude alcaftadine was stirred at a temperature in the range of 0° C. to 50° C. for a period of 30 minutes to 8 hours.

6. The process according to claim 4, wherein the organic solvent is an ether solvent selected from the group consisting of tetrahydrofuran, dioxane, diethyl ether, diisopropyl ether, dibutyl ether, methyl tertiary butyl ether, methyl ethyl ether, methyl isobutyl ether and mixture(s) thereof.

7. The process according to claim 4, wherein the β-crystalline form of alcaftadine is isolated by the steps of filtration, centrifugation, washing, drying or combinations thereof.

8. The process according to claim 7, wherein the isolated β-crystalline form of alcaftadine is dried at a temperature in the range of 40° C. to 110° C. for a period of 2 hours to 12 hours under reduced pressure.

* * * * *